US008530222B2

(12) United States Patent
Izumori et al.

(10) Patent No.: US 8,530,222 B2
(45) Date of Patent: Sep. 10, 2013

(54) MICROORGANISM WITH ABILITY TO PRODUCE DEOXY POLYOL DEHYDROGENASE AND USE THEREOF

(75) Inventors: Ken Izumori, Kagawa (JP); Kenji Morimoto, Kagawa (JP); Goro Takata, Kagawa (JP); Masaaki Tokuda, Kagawa (JP); Yoshio Tsujisaka, Kagawa (JP); Kei Takeshita, Kagawa (JP); Keiji Tsusaki, Okayama (JP); Kazuhiro Okuma, Itami (JP)

(73) Assignees: National University Corporation Kagawa University, Takamatsu-shi, Kagawa (JP); Rare Sugar Production Technical Research Laboratories, LLC., Kita-gun, Kagawa (JP); Matsutani Chemical Industry Co., Ltd., Itami-shi, Hyogo (JP)

( * ) Notice: Subject to any disclaimer, the term of this patent is extended or adjusted under 35 U.S.C. 154(b) by 859 days.

(21) Appl. No.: 12/515,602

(22) PCT Filed: Mar. 27, 2007

(86) PCT No.: PCT/JP2007/056456
§ 371 (c)(1),
(2), (4) Date: Mar. 5, 2010

(87) PCT Pub. No.: WO2008/062570
PCT Pub. Date: May 29, 2008

(65) Prior Publication Data
US 2010/0167350 A1    Jul. 1, 2010

(30) Foreign Application Priority Data
Nov. 20, 2006  (JP) ................................. 2006-313672

(51) Int. Cl.
*C12N 1/20*        (2006.01)
(52) U.S. Cl.
USPC .......................... 435/252.1; 435/190; 435/72
(58) Field of Classification Search
None
See application file for complete search history.

(56) References Cited

PUBLICATIONS

Taylor et al., Biochem. J. (1974) vol. 141, pp. 693-700.*
Fromm, J. Biological Chem. (1958) vol. 233, pp. 1049-1052.*
Dothie et al., Biochem. J. (1985) vol. 230, pp. 569-578.*

* cited by examiner

*Primary Examiner* — Irene Marx
(74) *Attorney, Agent, or Firm* — Westerman, Hattori, Daniels & Adrian, LLP

(57) ABSTRACT

Problem: To provide a microorganism with an ability to produce deoxy polyol dehydrogenase.
Means for Resolution: A microorganism belonging to genus *Enterobacter* with an ability to produce a dehydrogenase for deoxy polyol of the same structure at the positions C2 and C3 as that of ribitol or L-iditol. The bacterial cell IK7 of the genus *Enterobacter* (accession No. NITE P-271). A method for producing deoxy ketose comprising allowing a culture containing the deoxy polyol dehydrogenase obtained by the culturing of the microorganism of the invention or allowing the deoxy polyol dehydrogenase to react with a solution containing deoxy polyol of the same structure at the positions C2 and C3 as that of ribitol or L-iditol to oxidize deoxy polyol to produce the corresponding deoxy ketose and then collecting the deoxy ketose. The deoxy polyol is 1-deoxy-D-allitol, while the corresponding deoxy ketose is 1-deoxy-L-psicose. Otherwise, the deoxy polyol is L-rhamnitol, while the corresponding deoxy ketose is 1-deoxy-L-fructose.

3 Claims, 3 Drawing Sheets

MICROORGANISM WITH ABILITY TO PRODUCE DEOXY POLYOL DEHYDROGENASE AND USE THEREOF

TECHNICAL FIELD

The present invention relates to a microorganism with an ability to produce deoxy polyol dehydrogenase and the use thereof. More specifically, the invention relates to a method for producing deoxy ketose comprising oxidizing deoxy polyol using an enzyme produced by a microorganism of the genus *Enterobacter* and with an ability to produce deoxy polyol dehydrogenase, to produce the corresponding deoxy ketose and collecting the resulting deoxy ketose, as well as the collected deoxy ketose.

BACKGROUND ART 34 types of monosaccharides with 6 carbon atoms (hexose) exist in total, including 16 types of aldose, 8 types of ketose and 10 types of sugar alcohol. Aldose abundantly existing generally in the natural kingdom includes 6 types of aldose, namely D-glucose, D-galactose, D-mannose, D-ribose, D-xylose and L-arabinose, and other aldose types except those described above are designated as rare sugars. As the ketose, D-fructose exists, so other ketose types are designated as rare sugars. Other ketose types include D-tagatose, D-psicose, D-sorbose, L-fructose, L-psicose, L-tagatose and L-sorbose. Additionally, sugar alcohol is produced by reducing monosaccharides. In the natural kingdom, D-sorbitol exists relatively abundantly but other sugar alcohol types are quantitatively less. Therefore, such sugar alcohol types are designated as rare sugars. Demands toward such various types of rare sugars are emerging, so it is desired to establish a method for stably producing such sugars.

The method for producing such sugars may be performed by approaches of organic chemistry or by biochemical approaches. Regarding an enzymatic sugar conversion process which is carried out as one biochemical approach, patent reference 1 discloses inventions relating to ribitol dehydrogenase oxidizing ribitol in the co-presence of NAD+ to D-ribulose or reducing D-ribulose in the co-presence of NADH to ribitol, and a method for producing the same, as well as a microorganism generating the same, namely *Enterobacter aglomerans* 221e (FERM BP-4700), and a method for producing ketose or sugar alcohol using the enzyme or a microorganism with the enzyme activity.
Patent reference 1: JP-A-8-56659

DISCLOSURE OF THE INVENTION

Problems that the Invention is to Solve

It has been strongly desired to establish a method for producing sugars of various types as many as possible, by using enzymes of types of a number as small as possible in industrially producing sugars. With attention focused on enzymes reacting with sugars of types as many as possible, specifically sugar alcohol dehydrogenase, it should necessarily be done to screen a wide variety of microorganisms generating such enzyme. Therefore, it is an object of the invention to provide a novel microorganism generating a deoxy polyol dehydrogenase reactive with various types of sugars. Additionally, it is an object of the invention to produce various types of rare sugars readily by allowing the microorganism or the deoxy polyol dehydrogenase to react with a solution containing deoxy polyol as the substrate and generating the corresponding deoxy ketose.

More specifically, it is an object of the invention to provide a novel microorganism generating a deoxy polyol dehydrogenase involved in the conversion of L-rhamnitol to 1-deoxy-L-fructose or the conversion of 1-deoxy D-allitol to 1-deoxy-D-psicose, as well as a method for producing deoxy ketose using the enzyme or a microorganism with the enzyme activity, and a novel deoxy ketose.

Means for Solving the Problems

The gist of the invention resides in a microorganism with an ability to produce deoxy polyol dehydrogenase as described below in (1) through (5).

(1) A microorganism belonging to *Enterobacter*, which has an ability to produce a dehydrogenase for deoxy polyol of the same structure at the positions C2 and C3 as that of ribitol or L-iditol.
(2) A microorganism described in (1), which belongs to *Enterobacter aerogenes*.
(3) A microorganism described in (1) or (2), which is a bacterial strain IK7 (accession No. NITE BP-271) of the genus *Enterobacter*.
(4) A microorganism described in (1), (2) or (3), where the deoxy polyol is 1-deoxy D-allitol.
(5) A microorganism described in (1), (2) or (3), where the deoxy polyol is L-rhamnitol.

The gist of the invention resides in a method for producing deoxy ketose as described below in (6) to (10).
(6) A method for producing deoxy ketose, comprising allowing a culture containing the deoxy polyol dehydrogenase obtained by culturing any microorganism according to claims 1 through 4 or allowing the deoxy polyol dehydrogenase to react with a solution containing deoxy polyol of the same structure at the positions C2 and C3 as that of ribitol or L-iditol, to oxidize the deoxy polyol to produce the corresponding deoxy ketose and then collecting the deoxy ketose.
(7) A method for producing deoxy ketose as described in (6), where the deoxy polyol dehydrogenase is immobilized for reaction therewith.
(8) A method for producing deoxy ketose described in (6) or (7), where the deoxy polyol is 1-deoxy D-allitol and the corresponding deoxy ketose is 1-deoxy-D-psicose.
(9) A method for producing deoxy ketose described in (6) or (7), where the deoxy polyol is L-rhamnitol and the corresponding deoxy ketose is 1-deoxy-L-fructose.
(10) A method for producing deoxy ketose described above in (9), where the solution containing L-rhamnitol is a reaction mixture containing L-rhamnitol as obtained by reducing L-rhamnose.

The gist of the invention resides in a novel compound described below in (11) and (12).
(11) 1-Deoxy-L-fructose.
(12) 1-Deoxy-L-fructose described in (11), as obtained by allowing a bacterial cell with an ability to produce deoxy polyol dehydrogenase as obtained by culturing the bacterial strain IK7 (accession No. NITE BP-271) of the genus *Enterobacter* to react with a solution containing L-rhamnitol to oxidize L-rhamnitol, to produce 1-deoxy-L-fructose.

Advantages of the Invention

In accordance with the invention, a novel microorganism generating a deoxy polyol dehydrogenase reactive with various types of sugars can be provided. In accordance with the invention, additionally, rare sugars of various types can readily be produced by allowing the deoxy polyol dehydrogenase to react with a solution containing the substrate deoxy polyol to produce the corresponding deoxy ketose. In accordance with the invention, more specifically, there can be provided a novel microorganism generating a deoxy polyol dehydrogenase involved in the conversion of L-rhamnitol to 1-deoxy-L-fructose, as well as a method for producing deoxy ketose using the enzyme or a microorganism with the enzyme activity, and a novel deoxy ketose (1-deoxy-L-fructose, etc.).

BRIEF DESCRIPTION OF THE DRAWINGS

FIG. 3 13C NMR analysis results of purified 1-deoxy-L-fructose.

BEST MODE FOR CARRYING OUT THE INVENTION

Figure 1:
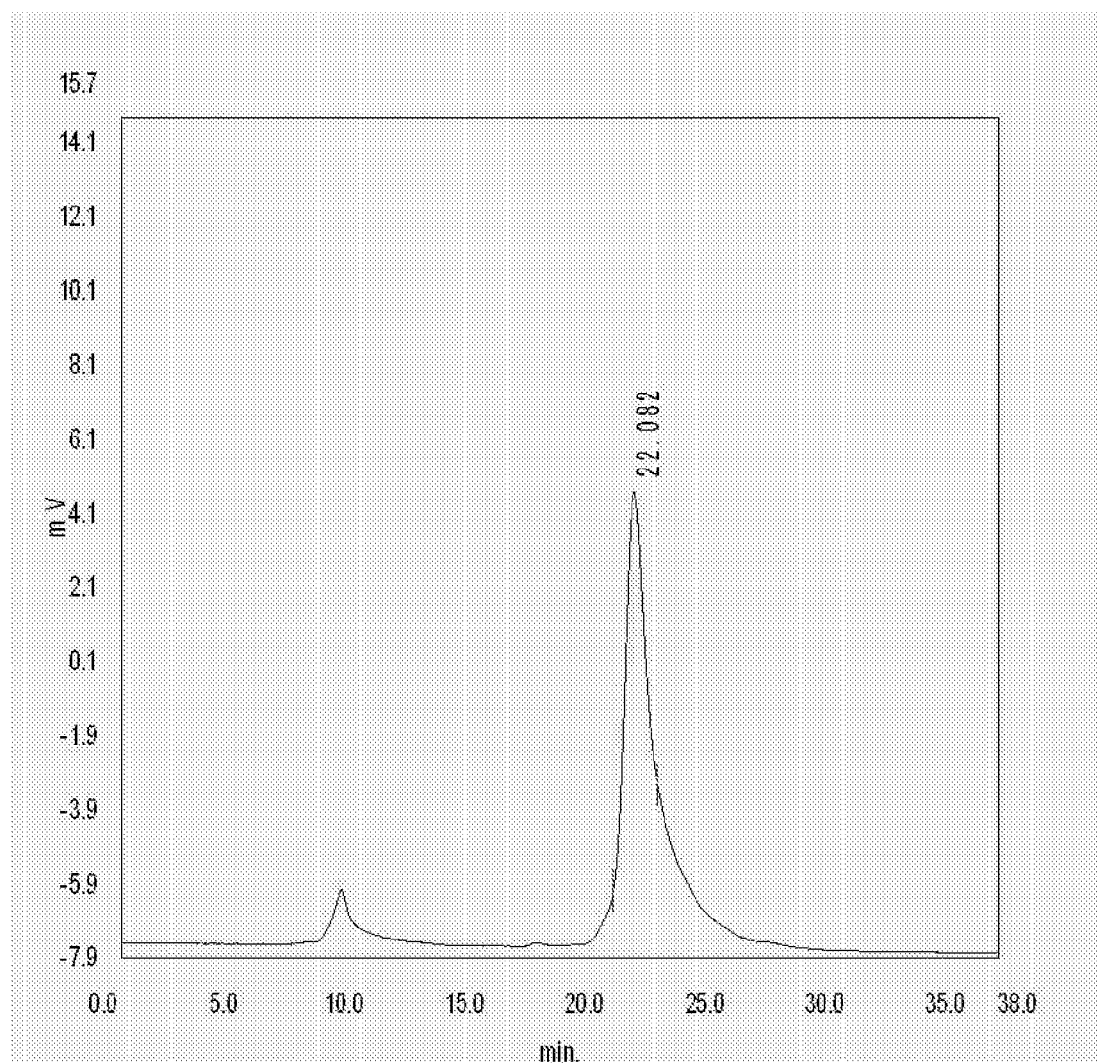
FIG. 1 HPLC analysis results of the substrate L-rhamnitol.

So as to solve the problems, the inventors made screenings for a wide variety of microorganisms generating an enzyme reactive with sugars of various types as many as possible, in particular the enzyme sugar alcohol dehydrogenase, with attention focused thereon. Consequently, the inventors found that *Enterobacter aerogenes* strain IK7 isolated in soils in a river bed in Miki-cho, Kida-gun, Kagawa, Japan was a novel microorganism of the genus *Enterobacter* and had a reaction with various types of polyol and an additional reaction with deoxy alcohol (deoxy polyol) to oxidize the deoxy polyol, to produce many types of ketose including deoxy ketose. The inventors found specifically that the oxidization reaction was extremely useful in generating various types of ketose, which could never readily been produced industrially. Thus, the invention has been achieved.

16SrRNA extracted from the bacterial strain was sequenced and the sequence thereof was compared with a plurality of known 16SrRNAs from other microorganisms. The data was 99-% identical to the sequence derived from *Enterobacter aerogenes*. Based on the evidence and other physiologically characteristic features shown in Table 1, it was concluded that the bacterial strain was *Enterobacter aerogenes*. The sequencing of the nucleotide sequence of a DNA fragment was done by the Sanger method (Molecular Cloning, Vol. 2, p. 13.3, 1989), PCR-based methods and the like.

Generally, the reaction is progressed with genomeLab DTCS Quick Start Kit (a sequencing kit containing fluorescence dideoxy terminator) manufactured by Beckman Coulter, for determining the nucleotide sequence with an automatic sequencer (CEQ 8000, etc.) of Beckman Coulter.

TABLE 1

| | |
|---|---|
| Gram staining | negative |
| Motility | none |
| Growth temperature | 37° C. (the growth is possible at 4 up to 40° C., preferably at 37° C.) |
| Oxygen demand | facultative anaerobic, preferably in an oxygen-supplied form |
| Morphology | rod |
| Urea decomposing property | negative |
| Ornithine decarboxylase | positive |
| Colonies at growing state | circle, protrusion, dryness, transparency, cream and white color |

[Culture Medium]
(Culturing is done at for example pH 5 to 9, preferably pH 6 to 8.5. Culturing is carried out under aerobic conditions such as shaking or aeration agitation)
 1. TSB (tryptic soy broth) culture medium 1 to 2%
  TSB: manufactured by Becton, Dickinson Company
 2. Meat extract culture medium
  (Meat extract (manufactured by Wako Pure Chemical Industry Co., Ltd.) 0.5%, polypeptone (manufactured by Wako Pure Chemical Industry Co., Ltd.) 0.5%, sodium chloride 0.5%, pH 7.0)
 3. Yeast extract culture medium
  (yeast extract (manufactured by Wako Pure Chemical Industry Co., Ltd.) 0.5%, polypeptone (manufactured by Wako Pure Chemical Industry Co., Ltd.) 0.5%, sodium chloride 0.5%, pH 7.0)
In case of an agar culture medium, agar is added to a final 2-% concentration.

The strain IK7 isolated by the inventors is a novel microorganism belonging to the genus *Enterobacter*, which was deposited domestically in Japan at Incorporated Administrative Agency, National Institute of Technology and Evaluation, Patent Microorganism Depositary, 2-5-8 Kamatari Kazusa, Kisarazu-shi, Chiba, Japan, for which an accession certificate was issued as an accession No. (NITE P-271) on Nov. 9, 2006. The bacterial strain was isolated in soils in a river flowing in Miki-cho, Kida-gun, Kagawa. In filing an international application, currently, it was requested to transfer the original deposit (NITE P-271) to an international depositary organization to which the original deposition was made. On Mar. 22, 2007, an accession certificate (NITE BP-271) was issued for the original deposit by the international depositary organization.

In accordance with the invention, not only the bacterial strain but also other bacterial strains with an ability to produce sugar alcohol dehydrogenase or variants thereof may appropriately be used.

Any synthetic or natural culture medium in which the microorganism can grow to produce sugar alcohol dehydrogenase may satisfactorily be used as the culture medium for culturing the microorganism of the invention. As a carbon source, one or two or more types selected from aldose, ketose, sugar alcohol and glycerol may appropriately be selected. As a nitrogen source, for example, inorganic nitrogen compounds such as ammonium salts, and nitrate salts as well as organic nitrogen-containing materials such as urea, corn steep liquor, casein, peptone, yeast extract and meat extract may be used. As an inorganic ingredient, for example, calcium salts, magnesium salts, potassium salts, sodium salts and phosphate salts may appropriately be used.

As the culture conditions, a temperature at which the microorganism can grow to produce the enzyme of the invention is suitable, which is generally about 4 to 40° C., preferably about 20 to 37° C. under conditions selected from pH of about 5 to 9, preferably pH of about 6 to 8.5. Culturing is carried out aerobically.

The microorganism of the invention is a microorganism of the genus *Enterobacter*, which has an ability to produce an enzyme activity dehydrogenizing deoxy polyol of the same structure at the positions C2 and C3 as that of ribitol or L-iditol. A microorganism belonging to *Enterobacter aerogenes*, more specifically an *Enterobacter* bacterial strain IK7 (accession No. NITE BP-271) is preferably listed. The microorganism of the invention exerts a polyol dehydrogenase activity to dehydrogenize 1- or 6-deoxyhexitol at the position 2 to produce 1- or 6-deoxyhexitol.

The sugar alcohol dehydrogenase activity produced by the microorganism of the genus *Enterobacter* in accordance with the invention can be utilized to produce various types of ketose with a keto group (C=O), because the enzyme oxidizes various types of sugar alcohols with the alcohol group bound to the carbon at the position 2 (H—C—OH) in a D-glycero coordination, including for example allitol, ribitol, L-rhamnitol, L-sorbitol, and L-mannitol, as substrates therefor. Hence, various types of sugars can be produced by using a single type of a microorganism, very advantageously industrially.

1-Deoxy-L-fructose can be produced by oxidizing L-rhamnitol as a substrate, which is a novel compound. Via similar oxidation of L-threitol and D-threitol, L-erythrulose and D-erythrulose, respectively can be produced, as verified by HPLC. These are novel methods for producing ketose types with 4 carbon atoms (see Table 2).

For the microorganism with the enzyme activity, the reaction from sugar alcohol to ketose requires aerobic conditions for example purging of oxygen or air, under agitation; while the reaction from ketose to sugar alcohol requires anaerobic conditions, for example environment with nitrogen and inactive gases, which should be retained.

In accordance with the invention, the microorganism with a deoxy polyol dehydrogenation activity as obtained by culturing the microorganism of the invention is allowed to react with a deoxy polyol-containing solution to oxidize the deoxy polyol to produce the corresponding deoxy ketose.

Additionally, the use of the microorganism after toluene treatment or after immobilization by known methods is optionally done. The reaction temperature is a temperature with no inactivation of the enzyme, for example 4 to 50° C., preferably 10 to 40° C. The reaction time is appropriately selected, depending on the level of the progress of the enzyme reaction. Generally, the reaction time is about 0.1 to 100 hours at an amount of the enzyme used at about 0.1 to 100 units per one gram of the solid substrate.

The reaction mixture thus obtained contains both sugar alcohol and ketose. The reaction mixture is optionally treated by general methods for removing insoluble matters, for example filtration and centrifugation, decoloring with active charcoal, desalting with ion exchange resins of H type and OH type, concentration and the preparation of the product into syrup-like products or drying the product into powdery products or finally preparing crystalline sugar into a crystal product. If necessary, further purification may be done optionally. For example, sugars at high purity can be readily obtained by fractionations by ion exchange column chromatography, active charcoal column chromatography, and silica gel column chromatography and by processes of decomposing and removing ketose with an alkali treatment. Various types of sugars thus obtained may advantageously be utilized in various uses such as sweeteners and quality modifiers for food industries, and raw materials and intermediates for pharmaceutical industries and chemical industries.

The invention is now described in detail in Examples. The invention is not limited by these Examples.

Example 1

Production of Microorganism with an Ability to Dehydrogenize Sugar Alcohol

Using for example sugar alcohol and glycerol as a carbon source, a culture broth was prepared (the optimal culture broth contained 1% D-mannitol as a carbon source in 2% TSB as a base); 100 ml each of the culture broth was placed in a 500-ml Erlenmeyer flask, for sterilization under heating (121° C., 15 minutes); *Enterobacter aerogenes* IK7 (accession No. NITE BP-271) was inoculated in the flask, for shaking culture at 37° C. and 120 rpm for 24 hours, to produce a bacterial cell containing a sugar alcohol dehydrogenase abundantly.

Example 2

Substrate Specificity

Using the microorganism with the sugar alcohol dehydrogenase activity as prepared by the method in Example 1, various sugar alcohols were used as a substrate to assay the oxidation activity thereof to ketose.

The bacterial cell (at a concentration of 30 as the absorbance at 600 nm) was shaken in 50 mM glycine NaOH buffer (pH 11) containing each of various sugar alcohols at 1% at 37° C. for one to 24 hours. Table 2 collectively shows substrates for conversion, products, reaction time and conversion ratios. Ketose types produced by these substrates were isolated by ion exchange column chromatography and were then verified by HPLC. The results are collectively shown in Table 2.

Since some types of polyols are wholly converted but other types of polyols are partially converted, the overall relative activity cannot generally be represented for clear comparison. As shown in the results, however, allitol was converted at 100% to D-psicose in about 2 hours; L-rhamnitol was converted at a 100% conversion ratio to 1-deoxy L-fructose and L-rhamnulose in about 12 hours; L-talitol L-sorbitol and L-mannitol were converted at a 100-% conversion ratio to L-tagatose, a mixture of L-fructose and D-sorbose and L-fructose, respectively in 24 hours. Concerning other polyol types as shown in Table 2, the microorganism has an ability to oxidize ribitol to D-ribulose, and to oxidize L-threitol to L-erythrulose.

TABLE 2

| Substrate | Main product | Reaction time (h) | Conversion ratio (%) |
|---|---|---|---|
| Allitol | D-psicose | 2 | 100 |
| L-Rhamnitol | 1-deoxy L-fructose and L-Rhamnulose | 12 | 100 |
| L-Talitol | L-tagatose | 24 | 100 |
| L-Sorbitol | L-fructose and D-sorbose | 24 | 100 |
| L-Mannitol | L-fructose | 24 | 100 |
| L-Iditol | L-sorbose | 24 | 92 |
| L-Arabitol | L-xylulose | 24 | 90 |
| Ribitol | D-ribulose | 24 | 60 |
| L-Threitol | L-erythrulose | 12 | 42 |
| D-Threitol | D-erythrulose | 12 | 40 |
| Erythritol | D-erythrulose | 12 | 38 |
| Xylitol | D-xylulose | 24 | 5 |

As apparently shown in the results of Table 2, the highest activity was exerted for allitol. The reaction modes for these sugar alcohols were examined. Consequently, these reaction modes are common. As one example, ribitol case is shown in Chemical formula 1.

[Composition formula 1]

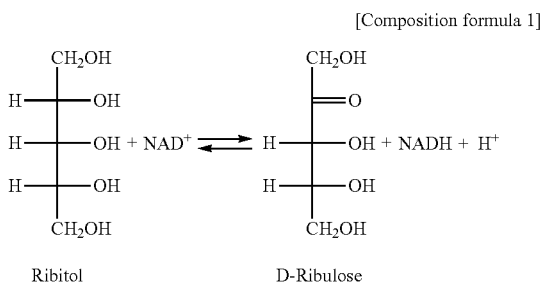

Ribitol     D-Ribulose

As apparently shown in Chemical formula 1, the bacterial cell of the invention has high activity for sugar alcohols with an alcohol group (H—C—OH) bound to the carbon at the position 2 in various polyols having D-glycero coordination. However, the activity is never exerted for D-iditol, D-mannitol and D-talitol, where the alcohol group bound to the carbon at the position 2 has L-glycero coordination.

Example 3

Production of Ketose from Sugar Alcohol

Using a microorganism with sugar alcohol dehydrogenase activity prepared by the method in Example 1, 1-deoxy L-fructose was prepared from L-rhamnitol.

[Chemical formula 2]

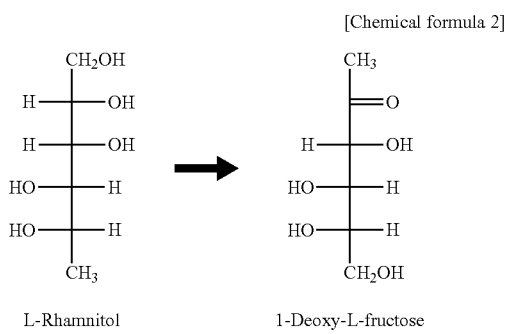

L-Rhamnitol     1-Deoxy-L-fructose

After completion of culturing, the culture was centrifuged to collect the bacterial cells, which were then washed twice with an appropriate volume of primary exchange water and were suspended in an appropriate volume of 50 mM Tris-HCl (pH 9.0) buffer. Based on the bacterial volume obtained from the culture volume, an appropriate reaction system is as follows.

Preferably, the bacterial cells are suspended in the buffer and the sugar solution in an L-tube (30-ml volume) under reaction conditions (reaction of washed bacterial cells) to a final concentration of 50 as the absorbance at 600 nm. As to the final bacterial cell concentration, the sugar concentration is possibly about 0.1 to 100. As to the concentration of L-rhamnitol, 0.1 to 20% L-rhamnitol can be converted. However, the conversion ratio to 1-deoxy L-fructose is the highest, and the optimal concentration is 10%. The reaction temperature is possibly 4 to 40° C. and is optimally 37° C. No agitation is necessary during the oxidation reaction, but shaking at about 50 rpm to retain aerobic conditions is preferable. The product is verified by centrifuging the reaction mixture obtained to remove insoluble matters and then analyzing the supernatant by high-performance liquid chromatography.

[Results]

Figure 2:
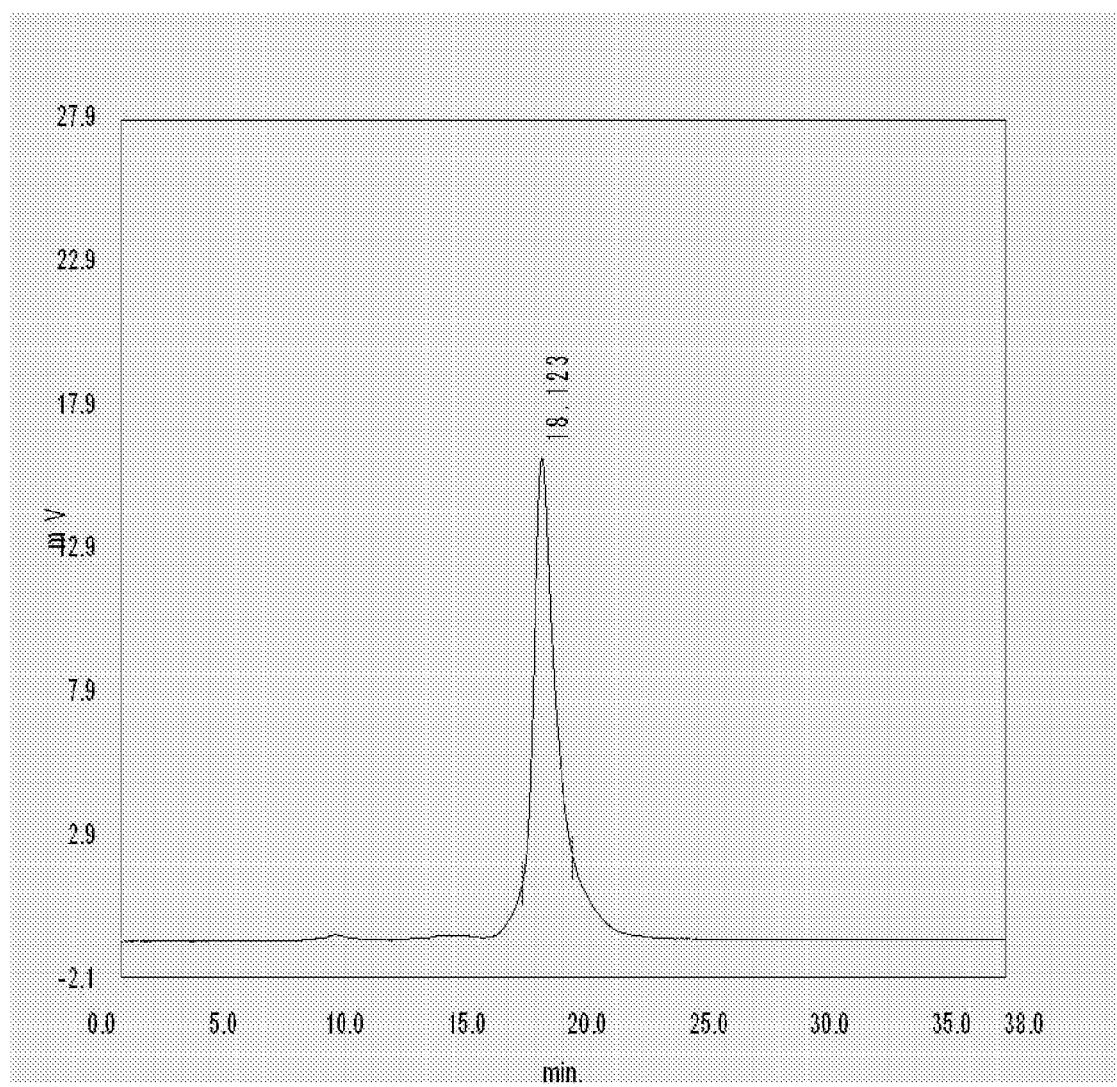
FIG. 2 HPLC analysis results of 1-deoxy-L-fructose resulting from the reaction of *Enterobacter* bacterial strain IK7 (accession No. NITE P-271) with the substrate L-rhamnitol.
Figure 3:
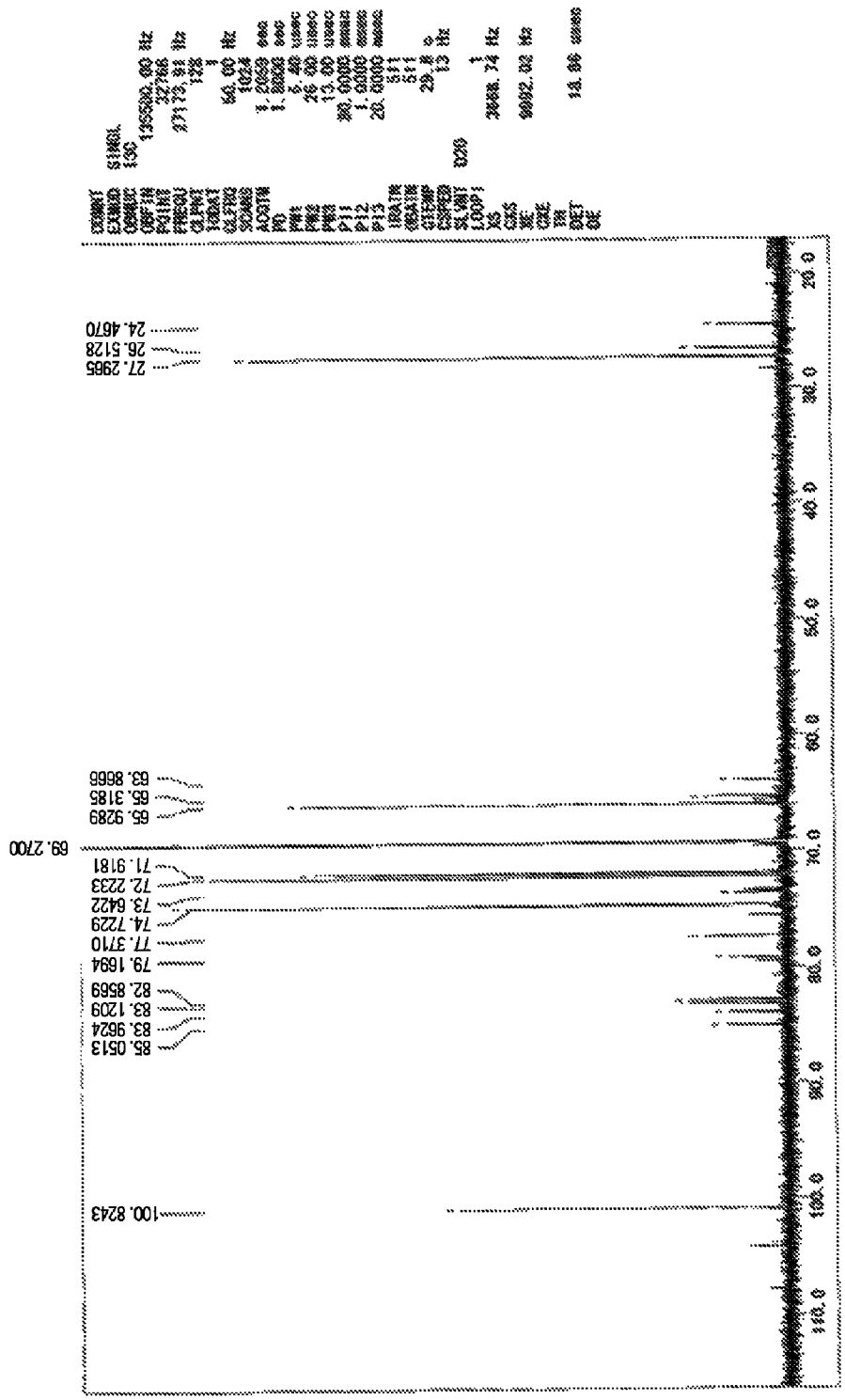

In 18 hours, 1-deoxy-L-fructose was obtained at maximum, indicating about 80% of L-rhamnitol is obtained as 1-deoxy-L-fructose. FIG. 1 shows the results of HPLC analysis of L-rhamnitol as a substrate. At about 22 minutes as the retention time, L-rhamnitol is observed. FIG. 2 shows the HPLC analysis results of 1-deoxy-L-fructose resulting from the reaction of the bacterial strain IK7 (accession No. NITE P-271) of the genus *Enterobacter* with a substrate L-rhamnitol. FIG. 3 shows the 13C NMR analysis results of the purified 1-deoxy-L-fructose.

Example 4

Production of 1-Deoxy L-Fructose Via Oxidation of 1-Deoxy L-Mannitol

Via a microbial reaction using *Enterobacter aerogenes* IK7 (accession No. NITE BP-271), 6-deoxy L-mannitol was oxidized to produce 1-deoxy L-fructose.

[Production of 6-Deoxy L-Mannitol Via Reduction of L-Rhamnose (6-Deoxy L-Mannose)]

Via a chemical reaction of 6-deoxy L-mannose, 6-deoxy L-mannitol was produced.

[Reduction Reaction with a Catalyst Raney-Nickel]

100 g of an aqueous 20% NaOH solution was added to 10 g of 50% Raney-nickel (manufactured by Wako Pure Chemical Industry Co., Ltd.). After addition, heating at 90° C. was done for one hour. After it was confirmed that gas generation stopped, the catalyst was washed with distilled water via decantation. Washing was continued until the wash solution reached pH 9.2.

24 g of Raney-nickel obtained by the method described above was added to 300 g of an aqueous solution containing 100 g of 6-deoxy L-mannose in a 1-L glass autoclave with an agitator and a thermometer, to which water was added to a final reaction volume of 600 g. So as to adjust the reaction mixture to pH 7, then, calcium carbonate was added. Reaction was progressed while the temperature was retained at 50° C.; the hydrogen pressure was retained at 12 kg/cm2 (gauge pressure); the agitation speed was retained at 700 rpm. The reaction mixture was analyzed by HPLC. Consequently, 6-deoxy L-mannose was decreased to 1% in the 8-hour reaction, to produce 6-deoxy L-mannitol.

[Production of Bacterial Cell Containing Sugar Alcohol Dehydrogenase]

In a culture broth sterilized (2% TSB (trypsin soy broth: Becton Dickinson company) as a base containing 1% D-mannitol as a carbon source), *Enterobacter aerogenes* IK7 (accession No. NITE BP-271) was inoculated, for culturing under shaking at 37° C. and 120 rpm for 24 hours, to produce a bacterial cell containing sugar alcohol dehydrogenase abundantly.

After completion of the culturing, the liquid culture was centrifuged to collect the bacterial cell, which was washed twice with an appropriate volume of primary exchange water, and then suspended in an appropriate volume of 50 mM Tris-HCl (pH 9.0) buffer. (This was designated as bacterial cell solution containing sugar alcohol dehydrogenase).

Using the prepared bacterial cell solution with a sugar alcohol dehydrogenase activity, 1-deoxy-L-fructose was produced from 1-deoxy L-mannitol.

In an L-tube (at a volume of 30 ml), 50 mM Tris-HCl (pH 9.0) buffer, the bacterial cell solution containing the sugar alcohol dehydrogenase (the final bacterial cell concentration was OD 20 as the absorbance at 600 nm) and 1-deoxy L-mannitol (final concentration of 10%) were placed and adjusted to OD 50 as the absorbance at 600 nm. Then, the mixture was kept warm at 37° C., for gentle shaking to prepare aerobic conditions. The product was confirmed by centrifuging the resulting reaction mixture to remove insoluble matters and analyzing the supernatant by high-performance liquid chromatography.

In 18 hours, 1-deoxy-L-fructose was obtained at maximum, at a yield corresponding to about 80% of 1-deoxy L-mannitol.

INDUSTRIAL APPLICABILITY

As described above, the bacterial strain IK7 (accession No. NITE BP-271) of the invention can advantageously be utilized for conversion of various types of sugars. The bacterial cell can advantageously be utilized for industrially producing rare sugars. In accordance with the invention, various types of rare sugars having been extremely hardly available conventionally can readily be produced, which may influence various fields including foods, cosmetics, pharmaceutical products and chemical industries. Thus, the invention has an industrially significant meaning.

The invention claimed is:

1. An isolated microorganism belonging to *Enterobacter*, which has the ability to produce a dehydrogenase which converts deoxy polyol to deoxy ketose having a keto group (C═O), wherein the deoxy polyol has the same structure at the positions C2 and C3 as that of ribitol or L-iditol and has an alcohol group (H—C—OH) bound to a carbon at the position 2, the alcohol group having D-glycero configuration, wherein the dehydrogenase does not convert D-iditol, D-mannitol and D-talitol to the deoxy ketose where the D-iditol, D-mannitol and D-talitol have an alcohol group bound to a carbon at the position 2, the alcohol group having L-glycero configuration, and wherein the isolated microorganism is the bacterial strain IK7 (accession No. NITE BP-271) of the genus *Enterobacter*.

2. The isolated microorganism according to claim 1, where the deoxy polyol is 1-deoxy D-allitol, and the deoxy ketose is 1-deoxy D-psicose.

3. The isolated microorganism according to claim 1, where the deoxy polyol is L-rhamnitol, and the deoxy ketose is the 1-deoxy-L-fructose.

* * * * *

UNITED STATES PATENT AND TRADEMARK OFFICE
CERTIFICATE OF CORRECTION

PATENT NO. : 8,530,222 B2  Page 1 of 1
APPLICATION NO. : 12/515602
DATED : September 10, 2013
INVENTOR(S) : Izumori et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1149 days.

Signed and Sealed this
Fifteenth Day of September, 2015

Michelle K. Lee
*Director of the United States Patent and Trademark Office*